United States Patent [19]

Casburn

[11] 4,159,021

[45] Jun. 26, 1979

[54] CHEST INCISION PROTECTOR

[76] Inventor: Robert T. Casburn, 1629 Calle Lindero, Lompoc, Calif. 93436

[21] Appl. No.: 850,932

[22] Filed: Nov. 14, 1977

[51] Int. Cl.² ............................................. A61B 19/00
[52] U.S. Cl. ................................. 128/149; 128/154
[58] Field of Search ............... 128/132 R, 132 D, 149, 128/171, 154

[56] References Cited

U.S. PATENT DOCUMENTS

| | | | |
|---|---|---|---|
| 2,505,720 | 4/1950 | Peiser et al. | 128/149 |
| 3,020,910 | 2/1962 | Ward | 128/132 R |
| 3,859,993 | 1/1975 | Bitner | 128/132 R |
| 3,976,066 | 4/1976 | McCartney | 128/154 |
| 4,000,737 | 1/1977 | Horn | 128/154 |

Primary Examiner—Lawrence W. Trapp
Attorney, Agent, or Firm—Harry W. Brelsford

[57] ABSTRACT

A vertical bar is placed over an incision and is spaced from the incision by upper and lower spider legs that have feet resting on the patient's body. The upper spider feet are held to the body by a neck strap and the lower feet by a waist strap. The bar is formed of telescoping sections to accommodate body movements and to adjust to patients of different size. The upper spider legs are V-shaped in elevation to permit the user to wear an open-neck shirt without the protector being visible.

3 Claims, 5 Drawing Figures

CHEST INCISION PROTECTOR

This invention relates to protectors for incisions on the chest and upper abdomen and has particular reference to such a protector held by straps to the body of the wearer.

BACKGROUND OF THE INVENTION

Major surgical procedures on the chest and upper abdomen usually result in long incisions that remain sensitive for weeks after they are surgically closed. While the patient is hospitalized a tent structure can keep bedding from touching the incision. With ambulatory patients, however, there is a severe problem of keeping clothing from touching the incision. Even the slightest touching of clothing causes severe irritation and much nervous distress until healing produces scar tissue that is tough and elastic.

This problem is aggravated by the absence of bandages over the incision. Current medical practive requires that the incision be open to air and free from bandages to reduce the danger of infection. The incision, therefore, is exposed to clothing and bed clothing from the very first hours after the operation.

Various body incision protectors have been devised over the years, and many of these rely on adhesives to hold the protector in place. The adhesives become irritants to the skin, and when the protectors are removed there are frequently spots of adhesive left on the skin that collect lint and catch on clothing and bedsheets, causing additional discomfort. Various tie-on protectors for feet, hands, and limbs have been devised, but no satisfactory incision protector has been provided for the patient's chest, trunk, or torso.

SUMMARY OF THE INVENTION

I have devised a strap-on incision protector for the chest and upper abdomen that avoids adhesives. Further, it permits maximum air circulation to the incision to keep it dry and promote healing. Additionally, it may be worn under clothing without being noticed by others. The device has a vertical telescoping bar spaced from the body by a pair of spider legs at each end, the tips of which rest on the body. The upper leg pair is held in place by a strap around the neck of the user, and the bottom spider leg pair is held by a horizontal strap around the waist of the user. All parts of the protector are made of lightweight material, preferably plastic.

DESCRIPTION

Various objects, advantages, and features of the invention will be apparent in the following description and claims considered together with the drawings forming an integral part of this application and in which:

Figure 1:
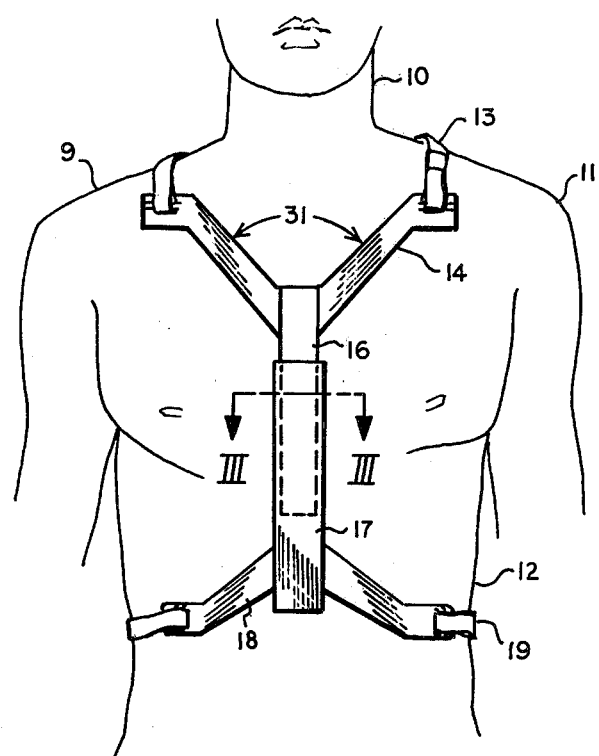
FIG. 1 is an elevation view of a person having a presently preferred embodiment of my protector attached to the person by a neck strap and a waistband.
Figure 2:
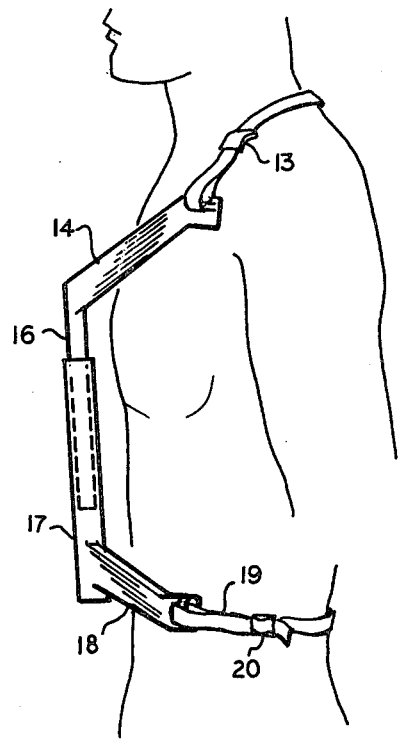
FIG. 2 is a side view of the person and the protector of FIG. 1.

Referring to FIGS. 1 and 2, a patient 9 has a neck 10 and a body 11 having a waist 12. Disposed about the neck 10 is a neck strap 13 supporting a pair of spider legs 14 connected to a vertical bar having an inner telescoping portion 16 and a lower telescoping portion 17. The bottom of the lower bar section 17 is supported by a pair of spider legs 18 to which is secured a waist strap 19.

Figure 3:
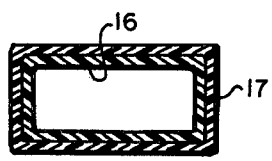
FIG. 3 is a sectional view on an enlarged scale along the line III—III of FIG. 1 showing the telescoping construction of the protector bar.
Figure 4:
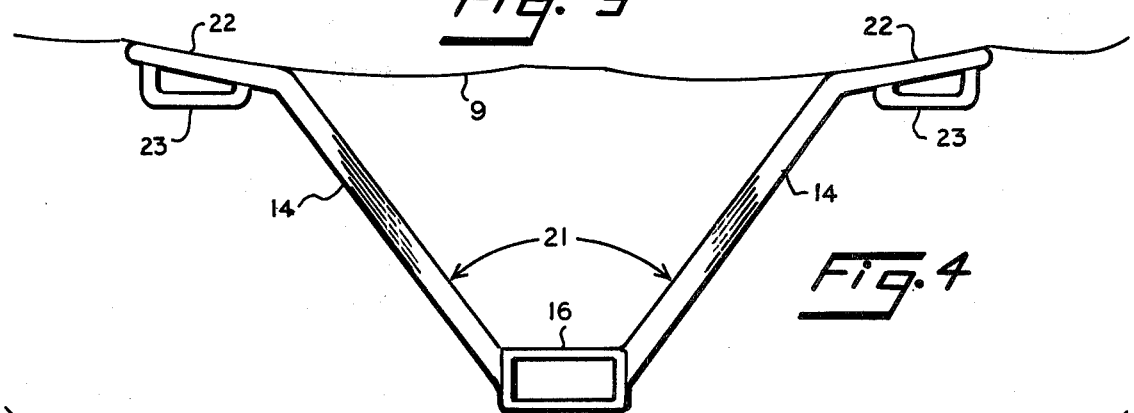
FIG. 4 is an end view on an enlarged scale of the upper pair of spider legs of the protector of FIG. 1.
Figure 5:
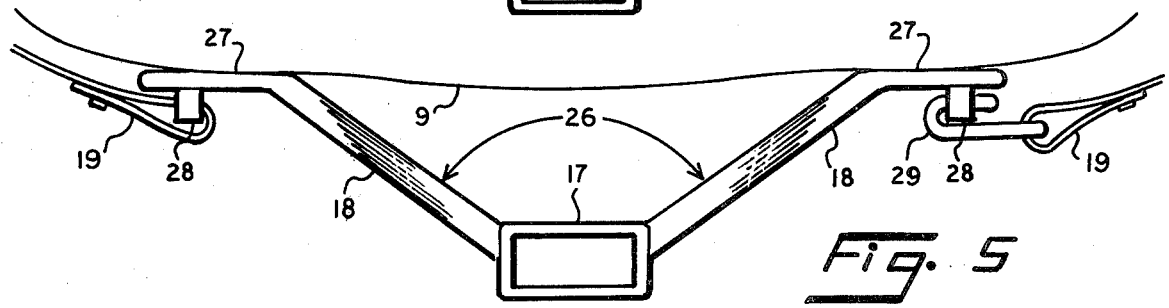
FIG. 5 is a bottom end view of the protector of FIG. 1 on an enlarged scale.

The details of construction of the protector are shown in FIGS. 3, 4, and 5, and in FIG. 3 it will be noted that the lower bar member 17 is hollow and telescopes over the exterior of the upper bar member 16, which is also hollow. This telescoping action allows not only for adjustment to fit the particular patient 9, but also permits the patient to bend over, and this shorter distance of the body from the upper chest to the waist is accommodated by the upper bar member 16 telescoping within the lower bar member 17.

Referring to FIG. 4, it will be noted that the spider legs 14 are connected to the upper bar member 16 at an angle 21, which causes the bar 16 to be spaced from the chest of the patient 9. The outer ends of the spider legs 14 terminate in flattened feet 22 to match the contour of the patient's chest. Projecting from the outer side of each of the feet 22 is a strap loop 23, which is the means of attachment of the neck strap 13 to the spider legs 14.

Referring to FIG. 5, it will be noted that the lower spider legs 18 are connected at a much larger angle 26 to the lower bar member 17 and thus space the bar 17 at a lesser distance from the body of the user. This difference in spacing is necessitated by the curvature of the upper chest and the upper spider legs 14 and must accommodate this curvature and lift the bar 16 a greater distance away from the body to achieve the same parallelism to the user's chest. This is best illustrated in FIG. 2. The lower spider legs 18 terminate in feet 27, which have loops 28 formed on the outer surface thereof. One end of the waist strap 19 may be fastened to one such loop 28. A hook may be inserted into the other loop 28, and the outer end of the hook 29 may be connected to the belt strap 19. The belt strap may have an adjustment buckle 20 as shown in FIG. 2.

It will be noted particularly with reference to FIG. 1 that in the elevation view there illustrated the spider legs 14 are formed at an angle 31 with respect to each other to create a V-shape. The spider legs 14 thus have a double angle, one illustrated in FIG. 1, and the other illustrated in FIG. 4. This V-shaped angle 31 permits the patient 9 to wear an opened-neck shirt and still not have the protector show.

The incision for open-heart surgery is normally vertical and normally toward the center of the chest; hence, it would usually be disposed approximately under the bar 16-17. This bar, accordingly, keeps clothing and any other objects from touching or rubbing against the incision and thus prevents itching and irritation. The use of the waist strap 19 holds the lower end of the bar 16-17 against the body, thereby preventing any pendulum effect of the bar. The protector is useful also for vertical incisions on the back of the chest. The straps are removable for washing.

The absence of adhesives in the use of this protector ensures maximum skin comfort for the patient and avoids the unpleasantness of stripping away strongly adhesive materials from the skin. This is particularly important after surgery wherein the chest is usually closely shaves; after a few days the sprouting hairs on a man's chest become extremely irritated by adhesives.

In actual use the protector has proven to be very comfortable. This is particularly true of heart patients, who are required to engage in regular walking exercise, thereby exposing the wound to rubbing of clothing unless it is protected. The protector accommodates the circulation of air to assist in the healing of the incision. The neck strap 13, as well as the waist strap 19, is preferably adjustable. The entire protector may be quickly installed by slipping the neck strap 13 over the head and wrapping the waistband 19 around the waist, hooking it by the hook 29 shown in FIG. 5. The telescoping construction of the bar 16-17 permits the use of the same protector on adults and on children. The spacing of the upper spider legs 14 is such that the protector may be readily used by women, the protector not touching the breast areas of the chest. The protector may be worn in bed, thereby preventing rubbing of bedding on the incision, and is strong enough to resist breakage if the sleeper should accidentally roll over on the protector. If seepage occurs from the incision, a necessary bandage may be applied to the incision and the protector may be disposed over the bandage.

I prefer to make the protector of lightweight materials. While lightweight metals could be used, I prefer at present to make it out of strong plastic with thin sections to thereby achieve minimum weight.

The invention has been described with reference to a presently preferred embodiment thereof as required by the statutes. It will be obvious to those skilled in the art that various modifications, variations, and improvements may be made in the device, and all such that fall within the true spirit and scope of the invention are included within the language of the following claims.

I claim:

1. A protector for incisions on the body of a wearer, comprising:
    (a) a generally vertical bar;
    (b) a pair of spider legs at each end of the bar, supporting the bar and spacing the bar from the body;
    (c) a neck strap secured to the outer ends of the upper spider legs;
    (d) and a waist strap secured to the outer ends of the lower spider legs;
said straps holding the protector to the body to space the bar over the wound and thus protect the wound from contact by clothing.

2. A protector as set forth in claim 1 wherein the vertical bar is formed of telescoping parts to allow for adjustment in length and to accommodate body movements.

3. A protector as set forth in claim 1 wherein at least the upper spider legs are Y-shaped in elevation so that the protector will not be visible to others when the user places an open-neck garment over the protector.

* * * * *